(12) United States Patent
Reinkensmeyer et al.

(10) Patent No.: US 6,880,487 B2
(45) Date of Patent: Apr. 19, 2005

(54) ROBOTIC DEVICE FOR LOCOMOTOR TRAINING

(75) Inventors: David J. Reinkensmeyer, Irvine, CA (US); Wojciech Timoszyk, Irvine, CA (US); Nikolas London, Cleveland, OH (US); Ray D. de Leon, Glendale, CA (US); V. Reggie Edgerton, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/117,409

(22) Filed: Apr. 5, 2002

(65) Prior Publication Data

US 2002/0157617 A1 Oct. 31, 2002

Related U.S. Application Data

(60) Provisional application No. 60/282,208, filed on Apr. 5, 2001.

(51) Int. Cl.$^7$ ............................................. A01K 15/02
(52) U.S. Cl. ..................... 119/700; 119/421; 119/728
(58) Field of Search ............................... 119/421, 728, 119/700, 703, 704, 674; 482/54; 601/5

(56) References Cited

U.S. PATENT DOCUMENTS

| | | | | |
|---|---|---|---|---|
| 5,100,127 A | * | 3/1992 | Melnick et al. ............. | 119/700 |
| 5,112,296 A | | 5/1992 | Beard et al. | |
| 5,466,213 A | | 11/1995 | Hogan et al. | |
| 5,667,461 A | * | 9/1997 | Hall ........................... | 482/69 |
| 5,704,881 A | * | 1/1998 | Dudley ....................... | 482/69 |
| 5,955,667 A | | 9/1999 | Fyfe | |
| 5,961,541 A | | 10/1999 | Ferrati | |
| 6,146,315 A | * | 11/2000 | Schonenberger ............ | 482/69 |
| 6,273,844 B1 | * | 8/2001 | Kelsey et al. ................ | 482/54 |
| 6,347,603 B1 | * | 2/2002 | Felger ......................... | 119/700 |
| 6,609,478 B1 | * | 8/2003 | Del Valle .................... | 119/703 |
| 6,666,831 B1 | * | 12/2003 | Edgerton et al. ........... | 600/587 |
| 2002/0010056 A1 | * | 1/2002 | Borsheim .................... | 482/66 |
| 2003/0064869 A1 | * | 4/2003 | Reinkensmeyer et al. .. | 482/100 |
| 2003/0196607 A1 | * | 10/2003 | Hong ........................ | 119/421 |

FOREIGN PATENT DOCUMENTS

| | | | | |
|---|---|---|---|---|
| DE | | 4103155 C1 | * 3/1992 | ............ A01K/1/03 |
| WO | PCT/CH99/00531 | | 5/2000 | |
| WO | PCT/US00/22966 | | 3/2001 | |

OTHER PUBLICATIONS

*Society for Neuroscience Abstracts* 2001,297.19, Use of Robots to Assess the Recovery of Hindlimb Movements and Weight Bearing During Stepping in Spinal Cord–Injured Adult Rats, de Leon et al.
*Society for Neuroscience Abstract* 2001, 297.20, The Lumbosacral Spinal Cord Adapts to Robotic Loading During Stance, Timoszyk et al.
*Society for Neuroscience Abstracts* vol. 24, 1998, 773.4 Automated Assay of Functional Motor Recovert Due to Intracisternal Growth Factors, Hogan et al.

(Continued)

*Primary Examiner*—Robert P. Swiatek
(74) *Attorney, Agent, or Firm*—Fulbright & Jaworski

(57) ABSTRACT

A robotic system and method for locomotion assessment and training of a mammal, exemplified by a rodent. A neurologically impaired animal is suspended over a moving surface in a harness, and the animal's hindlimbs are connected to robotic arms that apply force to the hindlimbs or measure limb movement characteristics. The moving surface can be a physical or virtual surface. A single robotic mechanism comprising two robotic arms can simultaneously apply force, measure limb movement, and provide a virtual surface. Manual or automatic adjustment of load support allows the mammal to step at varying body weight loads.

32 Claims, 11 Drawing Sheets

OTHER PUBLICATIONS

*Society for Neuroscience Abstracts* 2001, 260.14, Development of a Robotic System for Training Hindlimb Stepping in Spinally Transected Rats, London et al.

*International Conference on Rototics & Automation*, Apr. 2000, pp 2889–2894, A Robotic Stepper for Retraining Locomotion in Spinal–Injured Rodents, Reinkensmeyer et al.

*J. Rehab. Researcha and Development*, 37: 693–700 (2000) Treatdmill Training of Paraplegic Patients Using a Robotic Orthosis, G. Colombo et al.

*Society for Neuroscience Abstracts* 2000, Development of a Robotic System for Training Hindlimb Stepping in Spinally Transected Rats, N.J.S.London et al.

*Society for Neuroscience Abstracts* 2000, 26:697 Locomotor Adaptations to Robot–applied force fields in Spinally Transected Rats.

*J. Rehab. Research and Development* 2000, 37: 701–708, A Mechanized Gait Trainer for Restoration of Gait, S. Hesse et al.

*Society for Neuroscience Abstracts* 2000, 26: 697 Robotic Quantification of Stepping By Spinally Transected Rats: Comparison of Virtual and Physical Treadmill Approaches, Reinkensmeyer et al.

*Proc. Of $1^{st}$ Workshop on Robot Motion and Control (RoMoCo)*, Kiekrz, Poland, 1999, 9–16, Towards Development of Robotic Aid for Rehabilitation of Locomotion–Impaired Subjects, Bejczy et al.

De Leon R D, Hodgson J A, Roy R R, Edgerton V R: "Locomotor Capacity Attributable to Step Training Versus Spontaneous Recovery After Spinalization in Adult Cats" The Journal of Neurophysiology, vol. 79, No. 3, Mar. 1998, pp. 1329–1340, XP002215712.

De Leon R D, Hodgson J A, Roy R R, Edgerton V R: "Retention of Hindlimb Stepping Ability in Adult spinal Cats After the Cessation of Step Training" The Journal of Neurophysiology, vol. 81, No. 1, Jan. 1999, pp. 85–94, XP002215713.

* cited by examiner

ROBOTIC DEVICE FOR LOCOMOTOR TRAINING

CROSS-REFERENCE TO RELATED APPLICATIONS

This application is based on provisional application No. 60/282,208, filed on Apr. 5, 2001.

STATEMENT REGARDING FEDERALLY SPONSORED RESEARCH OR DEVELOPMENT

This invention was made with Government Support under Grant No. NS16333, awarded by the National Institutes of Health. The Government has certain rights in this invention.

BACKGROUND

1. Field of Invention

The present invention relates generally to a robotic locomotor training device.

2. Related Art

In the U.S. alone, over 10,000 people experience a traumatic spinal cord injury each year, and over 200,000 people with spinal cord injury are alive (20). Paralysis of the legs is a common consequence of spinal cord injury, resulting in loss of walking ability. Recently, a new approach to rehabilitation called "body weight supported locomotion training" has shown promise (12, 14, 20, 34, 35, 37, 41, 42, 53, 54, 55, 56). The technique involves suspending a spinal cord injured subject in a harness above a treadmill and manually assisting movement of the legs in a walking pattern. The key characteristics of this technique are partial unloading of the limbs, and assistance of leg movements during stepping on a treadmill. The goal of this technique is to enhance residual locomotor control circuitry that resides in the spinal cord. It is hypothesized that by providing appropriate sensory input (i.e. that associated with the force, position, and touch sensors that remain in the legs) in a repetitive manner, the spinal cord can learn to generate motor output appropriate for stepping.

This new approach to locomotion training is supported by studies of spinal cord injured animals (10, 11, 17, 29, 36, 39, 40, 48, 49, 50, 51, 59). For example, weight supported treadmill training was found to significantly enhance hindlimb stepping ability of spinal cord transected cats, indicating that the lumbar spinal cord can learn to step (8, 14, 22, 23, 37). Based on such animal studies, body weight supported training has been developed as a treatment therapy for humans following spinal cord injury, stroke, and other neurological disorders that impair locomotor ability (18, 19, 21, 25, 26, 27, 31, 56, 57, 58).

Research results indicate that body weight supported training does improve stepping in spinal cord injured humans, and that body weight supported training is superior to conventional rehabilitation (3, 18, 21, 25, 26, 27, 31, 56, 57). Among the many reported positive effects of body weight supported training is an improved ability to step at faster treadmill speeds and an increased weight-bearing ability in the legs. Moreover, evidence indicates that body weight supported training can improve overground walking ability (4, 28, 57). Wernig et al. reported that 80% of acute and chronic spinal cord injured patients (n=87) progressed from wheelchair-bound to independent overground walking after receiving several weeks of body weight supported treadmill training (56). Further, these beneficial effects lasted up to 6 years after the completion of training (57).

The lumbar spinal cord can learn to stand and step in the absence of supraspinal input (2, 6, 9, 12, 14, 15, 22, 23, 24, 37, 41, 42, 45). The capacity of the spinal cord to learn, if appropriately trained, is an extremely important finding for tens of thousands of spinal cord injured patients, as it could mean the difference between being confined to a wheelchair or standing and taking steps. Understanding how to teach the spinal cord to step by providing effective training has immediate clinical application in itself. Moreover, effective body weight supported training can play a role in enhancing the efficacy of other potential therapeutic interventions for spinal cord injuries, such as cell growth, cell engineering and pharmacological treatments (16, 38, 44, 47, 60), by providing an assessment of walking ability following therapeutic intervention.

Locomotor training provides sensory input that is critical for learning to walk Several lines of evidence indicate that the modulation of sensory input from the legs during training plays a significant role in the reorganization of the spinal circuits that generate stepping (9,13, 22, 23, 24, 41, 52). It is generally agreed that load-related information and proprioceptive sensory information are critical variables that must be controlled during locomotor training if stepping ability is to be enhanced. However, optimal procedures for unloading the limbs and assisting limb movements during stepping remain to be determined. In particular, the degree of unloading, the requirement for an alternating gait, and the extent of physical assistance of limb movement are unknown.

It is assumed that partially unloading the limbs is the best approach for training primarily because coordinated stepping movements are difficult to elicit with full weight bearing using current weight support techniques. It is possible that loading the limbs close to or above normal levels may more reliably elicit weight-bearing extension, and, if done repetitively, enhance recovery of stepping. Also, continually adapting weight support levels to adjust loading may provide maximal stimulation of load-related sensory input and therefore, improve stepping. However, current weight support techniques mechanically control weight bearing by adjusting the height of a harness system that suspends the animal or patient. As a consequence, current techniques cannot provide greater than normal loading on the limbs or be rapidly adjusted to adapt to fluctuations in motor output levels.

An alternating walking pattern is typically enforced during locomotor training in spinal cord injured animals and humans. However, it is possible that assisting coordination may not be necessary to recover an alternating pattern. Imposing different patterns of gait during locomotor training can help determine the flexibility of the motor output patterns produced by the spinal cord.

Current training can be characterized as "assist-as-needed" based on the premise that the spinal cord should be allowed to control stepping as much as possible. However, it is possible that simply driving the legs through the appropriate stepping pattern provides the essential sensory input needed to train for this motor task. Alternatively, allowing the spinal cord to freely "explore" the stepping dynamics may be a more effective way for the spinal networks to acquire those dynamics. The generation of error signals appears to be critical for hindlimb withdrawal reflex learning in the spinal cord (30), and a similar phenomenon also may be important in teaching the spinal cord to generate complex motor behaviors such as stepping.

The current method of locomotor training in humans relies on teams of trainers that work as a unit to manually assist leg and trunk movements. Such training is labor-intensive and often imprecise. In cases of flaccid paralysis, trainers must generate and control all leg and trunk movements, acts that can require substantial force, and are called on to repeat these acts hundreds or even thousands of times within one training session of a single person. Manual assistance of the limbs of a small animal during treadmill training is even more difficult to achieve in part because manipulating small limbs cannot be performed in a consistent manner. Robotic systems such as the present invention can bring an unprecedented level of control to spinal locomotion training.

Robotics provides a means to precisely control sensory input during locomotion training. Modern robotic devices can achieve highly dexterous motion, as well as precise quantification of force and motion. These capabilities have made possible a new generation of technology that convincingly simulates and provides control over a wide range of dynamic environments. Dexterous robotic devices are currently being used to enhance neurological rehabilitation (47). Robotic devices for therapy of the hemiparetic arm have been successful in enhancing motor recovery following stroke, and in better assessing that recovery (1, 43, 46).

Treadmill training of human subjects after spinal cord injury also provides an intriguing target for robotic technology (5, 7, 24, 25, 26, 27, 28, 32, 33). Robotic technology could improve experimental control during treadmill training, leading to a better understanding and optimization of training. Robotic technology could also provide a means to quantify in real-time the kinematics and kinetics of stepping. Ultimately, robotics could provide a way to both automate and monitor treadmill training in the clinic, reducing the cost of training and increasing its availability.

Developing robotic devices to provide precise control over body weight supported locomotion training requires an understanding of the engineering and physiological principles of robot-assisted step training. What is needed is a robotic device for test animals that allows experiments to be performed quickly and relatively inexpensively, with a capacity for testing a large number of training strategies. Such a device can enhance basic research of locomotion training and spinal cord learning, provide data on the engineering and physiological principles of robot-assisted step training for application to human therapy, and assess the efficacy of potential therapeutic interventions such as cell growth, cell engineering and pharmacological treatments.

An abstract by Hogan et al. (38) describes a small robot arm apparently used to "apply controlled forces to a rat's forepaw and continuously monitor the kinematics of limb movements". The rat was described as having a unilateral focal cortical lesion. Apparently, the robot simulated a "linear guide" that would guide the forelimb to a food pellet. However, the robot arm was not applied to the rat's hindlimb, and the robot was not directed to locomotion training.

SUMMARY

It is an object of the present invention to provide a robotic locomotion training system that is useful as a small-scale, well controlled test bed for evaluating the engineering and physiological principles to be used in a robotic step-trainer for spinal cord injured humans and for assessing the efficacy of potential therapeutic interventions.

Another object of the present invention is to provide a robotic locomotion training system for mammals that is capable of applying limb pressure and measuring limb movement in a repetitive manner while maintaining varying load conditions on the mammal.

It is also an object of the present invention to provide a method of locomotion training in which limb movement of a mammal can be repetitively assisted and assessed under varying load conditions.

The present invention is directed to a robotic system and method for locomotion assessment and training of a mammal. The robotic system comprises a moving surface for providing tactile sensory input to the mammal's limbs, a suspension assembly for suspending the mammal over the moving surface so that one or more limbs contact the surface, and a robotic mechanism for applying force to the limbs or for measuring limb movement characteristics of the suspended mammal. The moving surface can be a physical surface or a haptically simulated virtual surface. To provide varying load conditions, the suspension assembly can manually or automatically adjust the vertical position of the mammal relative to the moving surface. While the mammal is suspended over the moving surface, the robotic mechanism can separately or simultaneously apply force and measure limb movement.

The method of locomotion assessment and training provided by this invention comprises providing a moving surface for tactile sensory input, suspending the mammal over the moving surface so that one or more limbs contact the moving surface, and robotically applying force to the limbs or robotically measuring limb movement characteristics of the suspended mammal. Applying force and measuring limb movement can occur separately or simultaneously.

The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION

As used herein, the term "robotic" describes a mechanical device that can be programmed to automatically perform repetitious tasks involving manipulation and movement. The term "robotic arm" means an interconnecting set of links and joints moving with one or more degrees of freedom and capable of supporting a wrist socket such as a revolute joint and an end effector such as a gimbal.

The term "haptic simulation" refers to mimicking the sensation of an object by providing tactile sensory input. The phrase "haptic simulation of a moving surface" refers to simulating the tactile sensations of a moving surface.

The term "virtual surface" means an artificial moving surface perceived through haptic simulation. A limb "engages" a virtual surface when the limb receives haptic simulation of a moving surface.

As used herein, "load" means the amount of an animal's body weight being supported by, for example, a lever or the animal's limbs. The term "unloading" means supporting less than the animal's entire body weight.

The term "endpoint" in relation to robotic arms refers to the attachment point of a robotic arm to a limb. Endpoint position data can be collected in three dimensions (x, y, z position) for analysis.

Figure 1:
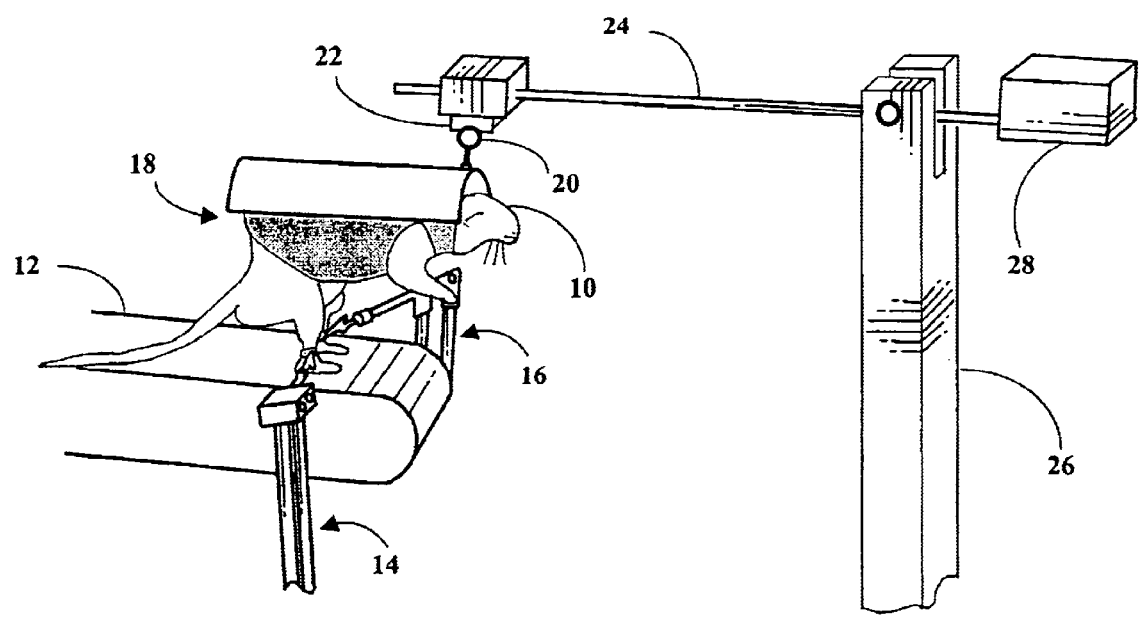
FIG. 1 is a sketch of a laboratory rodent undergoing locomotion training in accordance with an embodiment of this invention.

The present invention is directed to a robotic system and method for locomotion assessment and training of a mammal. Referring to FIG. 1, in accordance with this invention, a mammal 10 is suspended over a moving surface such as a treadmill 12, and a robotic mechanism such as one including robotic arms 14 and 16 is connected to one or more of the mammal's limbs.

With appropriate sizing of the equipment, the mammal can be any mammal with hindlegs including a human, a monkey or a cat, but preferably the mammal is about the size of a rat, ie., not more than about 12 inches (about 30.5 cm) long minus the tail. More particularly, the mammal is a laboratory rodent commonly used in experimental studies, for example a rat, a mouse or a hamster. Preferably, the mammal is a rat.

The moving surface can be a surface provided by devices well known in the art such as a motorized treadmill, a conveyor belt, or a moving walkway. Alternatively, the moving surface can be a virtual moving surface.

A suspension assembly supports the mammal's body over the moving surface. The mammal is vertically positioned above the moving surface so that one or more limbs of the animal contact the surface. Vertical position can be adjusted by raising and lowering the surface or, preferably, by raising and lowering the animal. By adjusting vertical position while the mammal's limbs contact the moving surface, body weight load on the limbs is altered.

In a specific embodiment of this invention, the suspension assembly comprises a manually adjustable counterweight system. Referring to FIG. 1, the system includes a harness 18, for holding the mammal's body, connected to a ball and socket assembly of a lockable ball joint 20. The harness 18 can be designed in a number of ways to hold the mammal in a manner that allows it to step. Together, the harness 18 and the lockable ball joint 20 act to orient the mammal's torso over the moving surface. The lockable ball joint 20 is connected to a single axis load cell 22. In turn, the load cell 22 is connected to a counterbalanced lever 24 pivotally mounted on a support structure 26 such that body weight load monitored by the load cell 22 can be manually adjusted by changing the position of a fixed weight 28 along the counterbalanced lever or by changing the fixed weight 28 to a fixed weight of different mass.

In another embodiment, the suspension assembly comprises an automatically adjustable, motorized support system including a harness connected to a lever through a load cell. The lever is rotatably mounted on a DC torque motor shaft such that motor torque adjusts load on the lever. A data acquisition card is connected to the load cell for measuring weight support. Weight support can be varied by controlling motor torque through a digital to analog conversion card receiving instructions from a suitably programmed computer.

Figure 2:
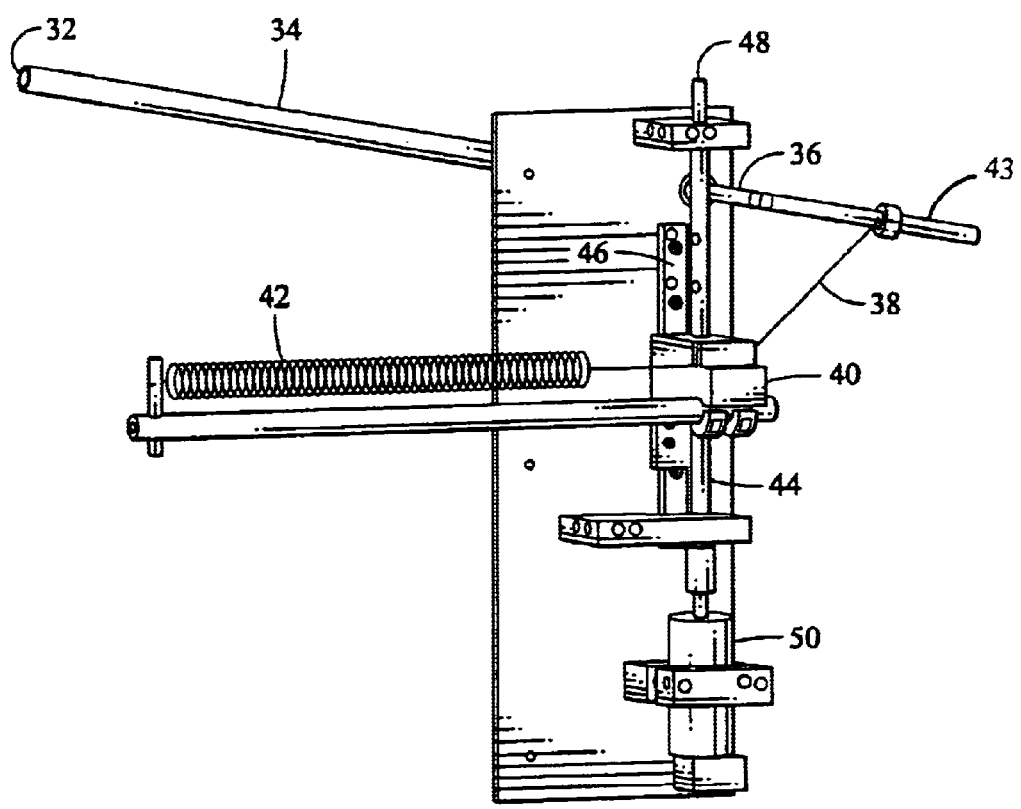
FIG. 2 is a view of a spring-actuated support system.

In a further embodiment, the suspension assembly comprises a spring-actuated support system. Referring to FIG. 2, the support system includes a harness connected to the end 32 of a load-bearing element in the form of a lever arm 34 which pivots on a pivot shaft 36. An animal's weight is partially counterbalanced by a force transmitting device in the form of a polyester rope 38 that is wound around a pulley (not shown) housed in a spring/pulley bracket 40 and kept in tension by a spring 42. The rope is attached to a tension-receiving element in the form of a second lever arm 43 that pivots on the pivot shaft. When the following conditions are met, the amount of upward force provided at the harness connection point is independent of the pitch angle of the lever arm 34: (1) the take-off point of the rope 38 on the pulley is directly below the axis of the pivot shaft 36; and (2) the spring 42 is not in tension when the end of the rope 38 is at the take-off point. The amount of upward force is increased by moving the spring/pulley bracket 40 down (this adds pretension to the spring 42, while leaving conditions (1) and (2) unchanged). This adjustment is made by turning a lead screw 44 which causes the spring/pulley bracket 40 to move on a linear bearing 46. The lead screw 44 can be turned with a crank handle attached to end 48 of the lead screw 44, or with a computer-controlled electric motor 50.

This spring-actuated support system is more complex than the simple counterweight system shown in FIG. 1, but has several advantages. In particular, the spring-actuated system has a lower inertia than the counterweight system. In addition, the inertia does not depend on the amount of body weight support provided, in contrast to the counterweight system. The system also has advantages over a simple spring counterbalance system in that it provides a constant force independent of the support lever angle, eliminating the "springiness" or resonance associated with most spring-based counterbalance systems. The spring-actuated system also has very low backdrive friction, while being capable of generating large forces to lift a rat. Finally, the amount of body weight support can be adjusted by driving the lead screw 44 either manually or with a computer-controlled motor.

In accordance with this invention, a robotic mechanism interacts with a mammal's limbs. The robotic mechanism can include a robotic force applicator for applying force to one or more of the limbs. Force can be applied to assist or resist limb stepping. Further, the robotic mechanism can include a robotic measuring apparatus for measuring limb movement characteristics such as limb position, limb velocity, stance duration, swing duration, and forces generated during stepping.

A single robotic mechanism can comprise both the force applicator and the measuring apparatus, performing their functions separately or simultaneously. In accordance with this invention, the single robotic mechanism can include two robotic arms, one for each hindlimb. For mammals such as rats whose hindlimb motion while stepping occurs primarily in the parasagittal plane, robotic arms with at least two degrees of freedom are sufficient to track limb motion.

Figure 3:
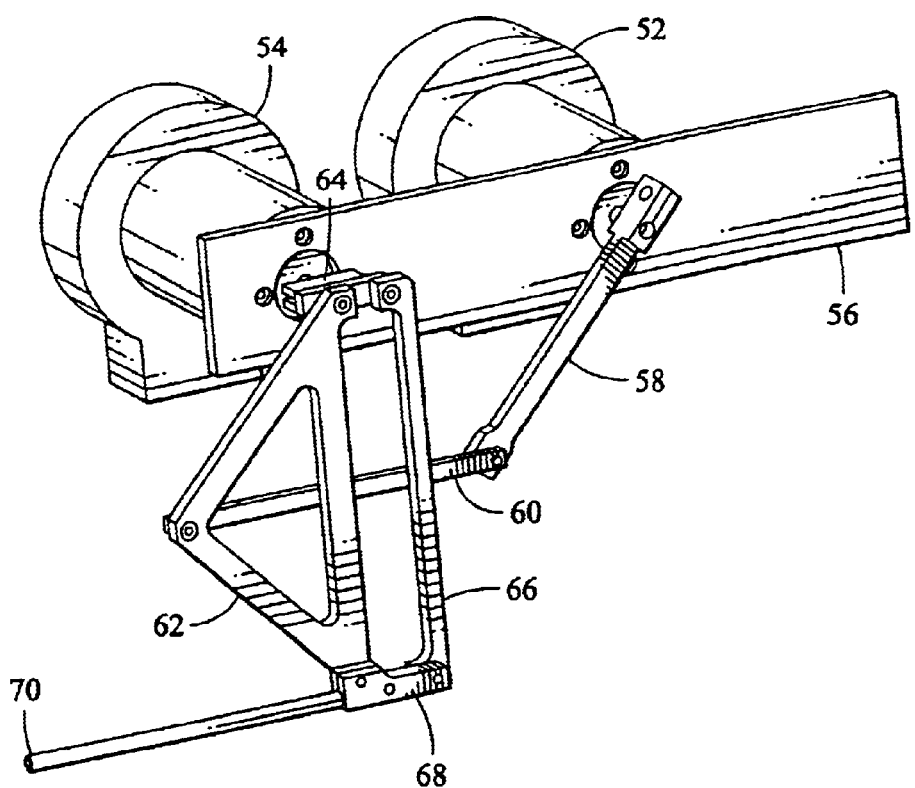
FIG. 3 is a view of a robotic arm with a seven-bar linkage.

In a specific embodiment, each robotic arm is a seven-bar linkage with two degrees of freedom. Referring to FIG. 3, each robotic arm includes two mechanically grounded brushless DC motors 52 and 54. Motor 52 is attached to a four-bar linkage consisting of ground link 56 and links 58, 60 and 62. Motor 54 is attached to a five-bar linkage consisting of ground link 56, links 62, 64 and 66, and end link 68. The two linkages share link 62, thereby constraining the device to planar, two degree-of-freedom motion. Tip 70 of the robot arm end link 68 can be attached to a mamma's limb through a revolute joint. The robotic arm can be programmed to apply forces to hindlimbs and to measure limb movement characteristics. One advantage of this robotic arm is low inertia and friction with substantial vertical and/or horizontal force at the tip 70, a result of mechanically grounding motors 52 and 54. Another advantage is that both motors are on the same side of the seven-bar linkage, leaving space for an animal to be placed between two mirror-symmetric robotic arms, one for each hindlimb. In a specific embodiment for training rats, the robotic arm has a workspace of about 5 inches horizontally and about 2 inches vertically, and provides about 5 gF resistance while generating up to 150 gF (a medium-sized rat weighs about 300 g).

Commercially available robotic arms can be applied to locomotion training of mammals. Suitable robotic arms can be programmed to apply forces to a mammal's limbs and to measure limb movement characteristics. One such commercially available robotic arm for locomotion training of a laboratory rodent is the Phantom 1.0 (SensAble Technologies, Inc.) which is a cable-driven, mechanical linkage having high fidelity force control and three degrees of freedom. A software development kit in C++ programming language, the General Haptic Open Software Toolkit (Ghost SDK 2.1 from SensAble Technologies, Inc.) is available for programming the Phantom 1.0. In addition to applying force and measuring limb movement, the Phantom 1.0 can be programmed to haptically simulate a variety of virtual objects.

Figure 4:
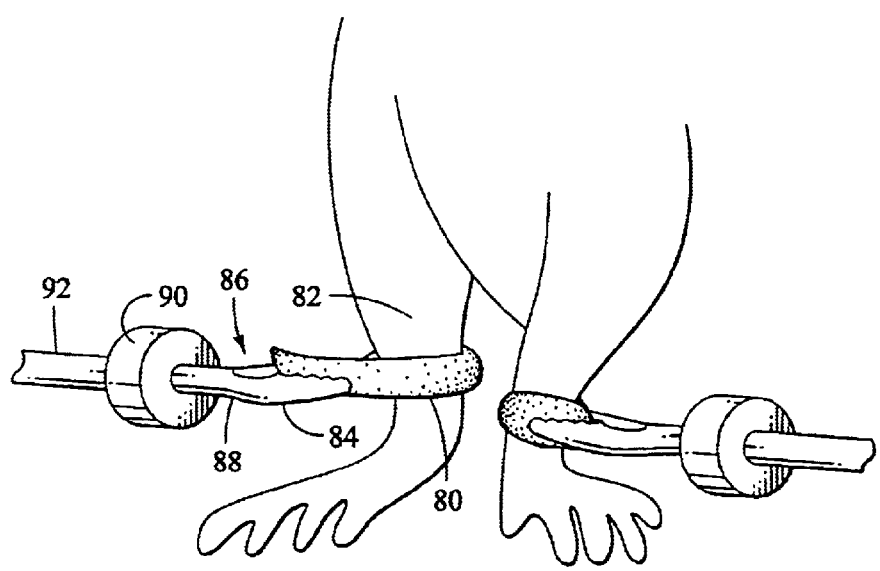
FIG. 4 is a sketch of rodent hindlimbs connected to robotic arm end links by means of neoprene cuffs.

A robotic arm can be connected to a mammal's limb by methods well known in the art. A preferred method of connecting a robotic arm to a rodent hindlimb is by means of a padded neoprene cuff 80 encircling the rodent's lower shank 82, as shown in FIG. 4. The cuff 80 can be made from neoprene straps and foam padding to provide a secure, non-irritating fit. The cuff 80 is dimensioned such that stepping can occur without restricting hindlimb movement. For a rat, a cuff of about 3 mm by about 30 mm is suitable. To connect the cuff 80 to the robotic arm, the jaw end 84 of an alligator clip 86 is fastened to the cuff 80 and the handle end 88 of the clip is connected to a revolute, ball bearing joint 90. In this figure, the revolute joint 90 is connected to the tip of robotic arm end link 92 such that the axis-of-rotation of the revolute joint 90 is co-linear with the longitudinal axis of the end link 92. In such configuration, the end link moves in a direction perpendicular to its longitudinal axis and parallel to the parasagittal plane of the rodent. In contrast, for an end link whose direction of movement is parallel to its longitudinal axis, such as end link 68 in FIG. 3, the revolute joint is connected so that the axis-of-rotation of the revolute joint is perpendicular to the end link's longitudinal axis.

The neoprene cuff method has the advantage of not restricting hindlimb movement yet providing precise control and measurement of ankle trajectory. Further, the method provides normal patterns of sensory input to be generated through the plantar surface of the paw during weight bearing, and minimizes elicitation of flexion withdrawal and scratch responses.

In accordance with the present invention, a mammal can be suspended over a virtual moving surface generated by a robotic haptic simulator. As the limbs of the suspended animal engage the virtual surface, a robotic force applicator can apply force to the limbs and, separately or simultaneously, a robotic measuring apparatus can measure limb movement characteristics.

Figure 5:
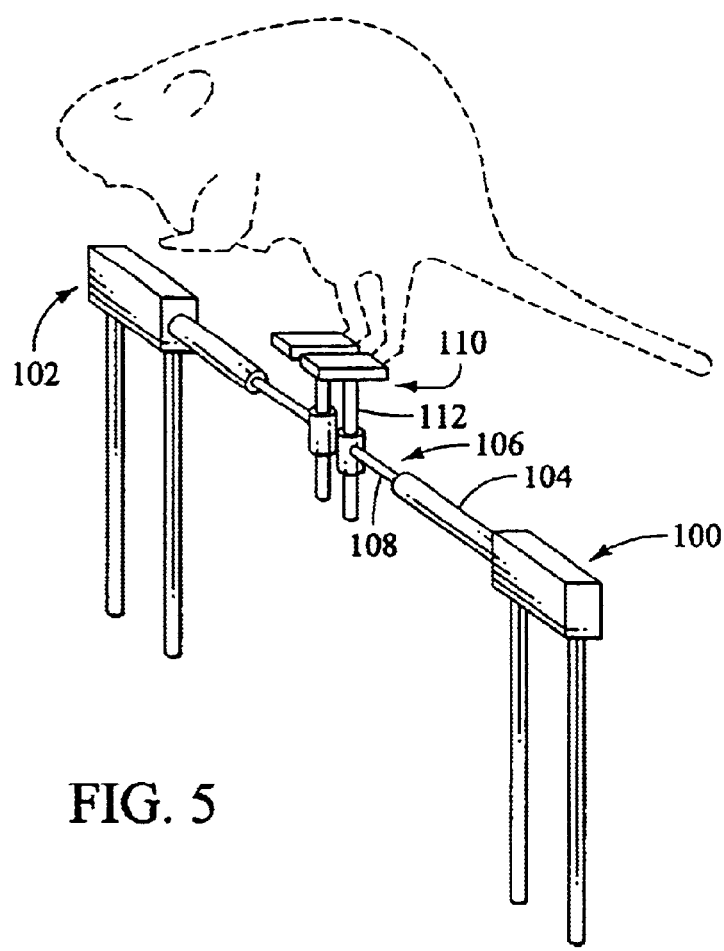
FIG. 5 shows a method of providing haptic simulation to a laboratory rodent by means of platforms that attach to the rodent's feet.
Figure 6:
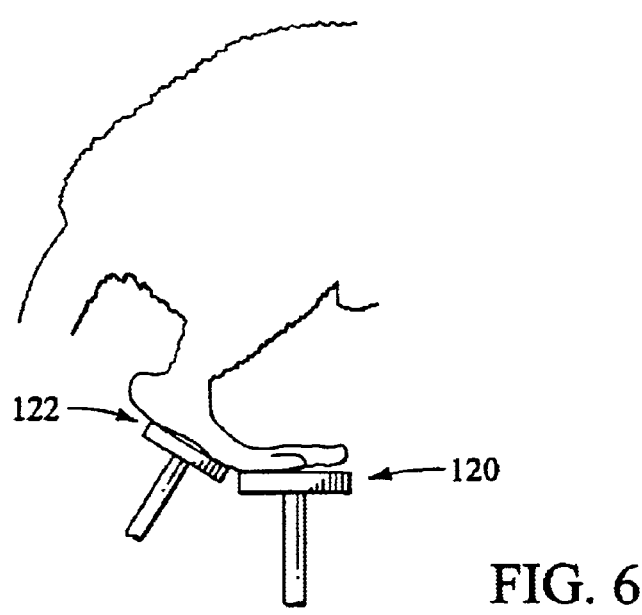
FIG. 6 is a sketch showing two positions for platform attachment to rodent feet.

One way of providing a mammal with a virtual moving surface or a stationary surface is to connect the mammal's hindlimbs to robotic arms programmed to haptically simulate a treadmill or a floor, respectively. In particular, each hindlimb can be connected to a robotic arm by means of a platform. Referring to FIG. 5, each robotic arm 100 and 102 has an end link 104 that is connected to a fixed joint 106 through a fixed joint handle 108. Attached to the fixed joint 106 is a rectangular platform 110 having an upper surface for contacting the mammal's foot and a handle 112 for connecting to the fixed joint 106. For a laboratory rodent, the platform 110 can be fabricated from PC board and dimensioned approximately the size of the rodent's toes. As shown in FIG. 6, the platform 110 can be placed under the rodent's foot in a forward position 120 for attachment to toes, or in a rearward position 122 for attachment to heel or ankle. Platforms can be attached to toes, heel or ankle with adhesive tape. Alternatively, the neoprene cuff method described herein is preferred when attaching robotic arms to the rodent's metatarsus or lower shank, Suitable robotic arms for providing a haptically simulated treadmill are those such as the Phantom 1.0 which can be programmed to haptically simulate a treadmill, apply forces to rodent hindlimbs, and collect robotic arm endpoint position data. When rodent hindlimbs are connected in the manner shown in FIG. 5, such robotic arms can simultaneously carry out these programmed activities.

Figure 7:
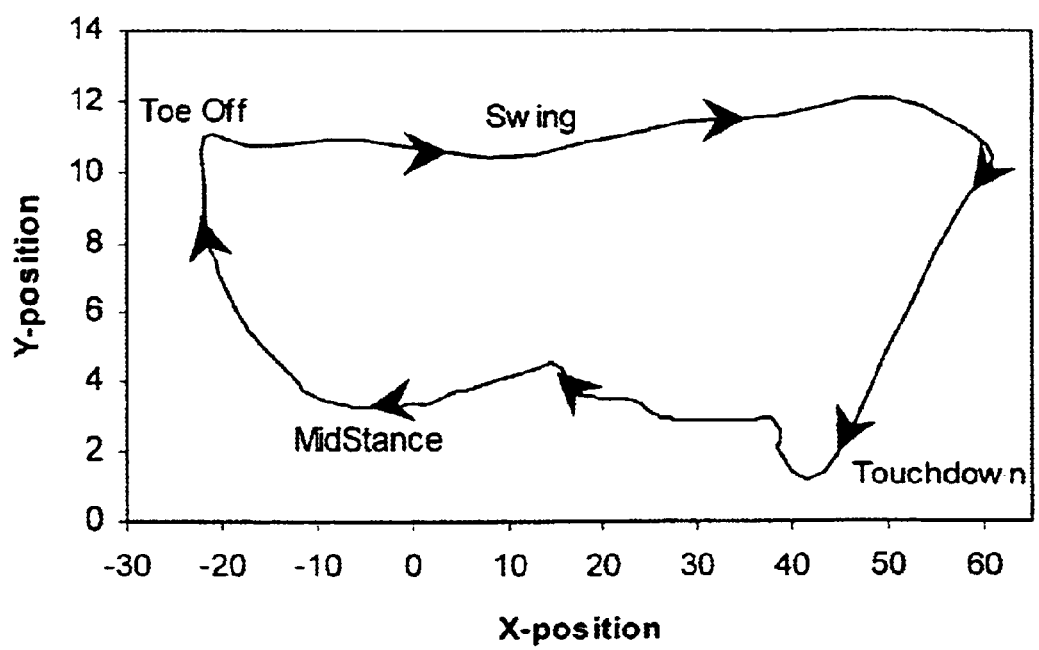
FIG. 7 is a graph showing a kinematic analysis of robotic arm—generated kinematic data obtained during bipedal hindlimb locomotion of a rat.

In practicing this invention, position data (x, y, z position) of the attachment point of robotic arms to rodent hindlimbs can be recorded by robotic arms and collected and analyzed by suitable computer software. FIG. 7 shows the trajectory of a shank recorded by the robot arm during one representative step cycle. Horizontal (X-position) and vertical (y-position) shank positions are displayed. Arrows indicate direction of movement, and key events in the step cycle such as touchdown, midstance, toe off and swing are indicated. Shank positions that correspond to the key events are detected by the computer software, and computer-detected events for every cycle are used to calculate kinematic variables such as extension, flexion, step length, step timing, step height and hindlimb coordination parameters. An ability to quickly analyze a large number of steps makes practical very robust statistical analyses of step characteristics.

Figure 8:
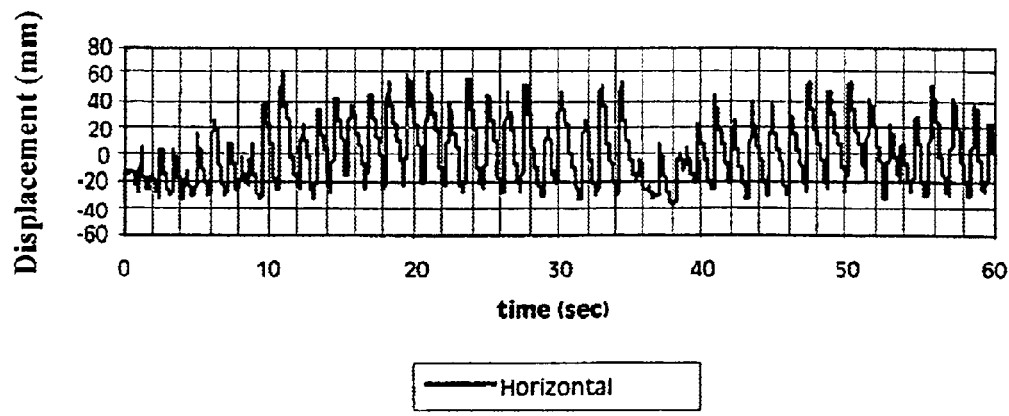
FIG. 8 is a graph showing the horizontal displacement of a rat shank during 60 seconds of stepping.
Figure 9:
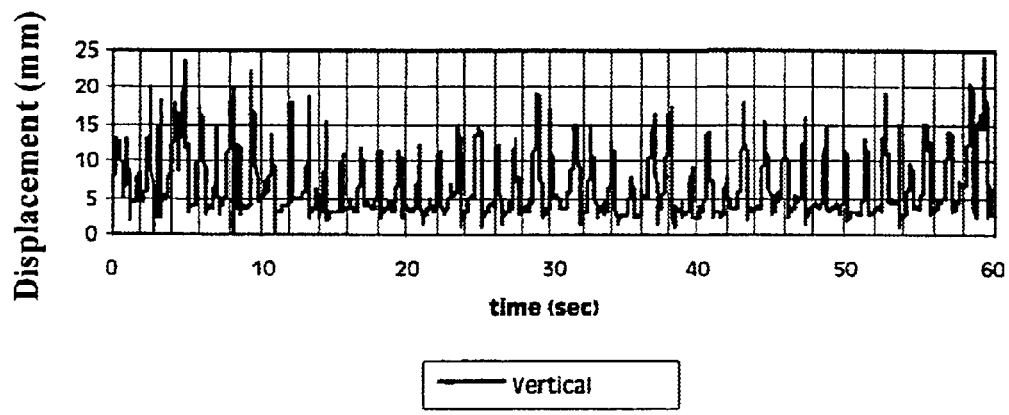
FIG. 9 is a graph showing the vertical displacement of a rat shank during 60 seconds of stepping.
Figure 10:
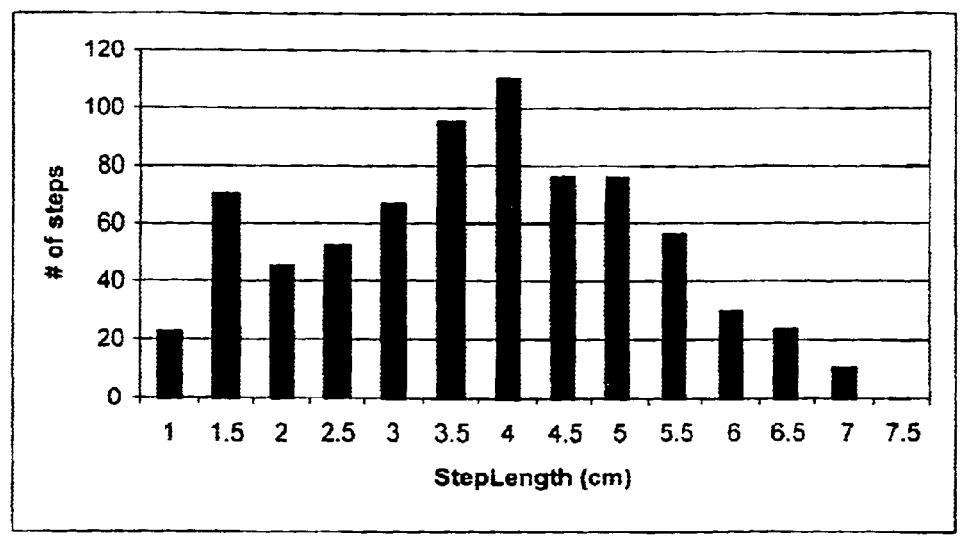
FIG. 10 is a histogram of step lengths for a rat during 3 minutes of stepping at three different treadmill speeds.

Kinematic analyses of robot-generated kinematic data during bipedal, hindlimb locomotion in a spinal injured rat are shown in FIGS. 8, 9 and 10. FIG. 8 shows the horizontal displacement of one shank during 60 seconds of stepping at a treadmill speed of about 11 cm/s and a load on the rat of about 25% body weight. FIG. 9 shows the vertical displacement of the shank under the same conditions. FIG. 10 shows a histogram of step lengths during 3 minutes of stepping at treadmill speeds of about 6 cm/s, about 11 cm/s and about 20 cm/s, at about 25% load. For these analyses, a total of seven-hundred-thirty-seven cycles were analyzed. Measuring and analyzing capability of the robot system is far greater than conventional kinematic film analyses primarily because positional data is recorded on-line making film digitization unnecessary. Thus, step cycle characteristics from hundreds of steps can be quantified from the robot data in a matter of minutes, a task that would take several weeks to complete using traditional digitizing kinematic analyses.

The present invention may be better understood by referring to the accompanying examples involving specific embodiments of this invention. These examples are intended for illustration purposes only and should not in any sense be construed as limiting the scope of the invention as defined in the claims appended hereto.

EXAMPLE 1

This example shows that training with the robotic locomotion system improves stepping of spinal transected rats.

Rats received complete spinal cord transections five days after birth and began training (two hours of training per week for eight weeks) shortly after weaning. The amount of weight support during training was adjusted to allow a load level on the hindlimbs that was equivalent to half of normal levels. During training over a moving surface provided by a conveyor belt, a Phantom 1.0 robotic arm was attached to each hindlimb shank by a neoprene cuff to record and quantify hindlimb trajectories. In this example, the robotic arms did riot apply assistive force during stepping. Instead, the arms moved passively with the hindlimbs.

Figure 11:
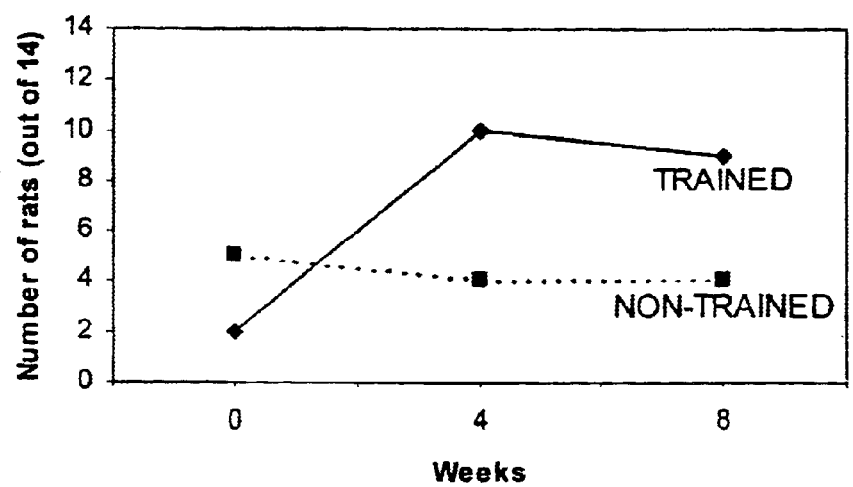
FIG. 11 is a graph comparing the stepping ability between trained and non-trained spinal cord injured rats.

A graph of stepping ability of trained and non-trained spinal transected rats is shown in FIG. 11. Each point on the graph represents the number of rats that successfully stepped on a certain week after training started. Successful stepping was defined as the ability to perform twenty consecutive steps with half normal load at a speed of about 11 cm/s. As shown by the solid line, the ability of trained rats to perform consistent stepping with half of normal weight bearing improved over 8 weeks of training. Moreover, training enhanced the recovery of partial weight-bearing stepping based on comparisons of locomotion between the trained rats and the non-trained rats (dotted line). An important finding, however, was that training with these loading conditions and with passive robots did not improve stepping at higher load levels. No significant differences were found between the trained and non-trained groups when locomotor performance with normal weight bearing was tested. These findings indicate that the rat spinal cord can learn to step with robotic linkages attached to the hindlimbs. Furthermore, the inability to step with full weight bearing in the trained animals suggests that weight-bearing stepping can be improved with more effective control over loading during stepping, i.e. adjusting load on a step-by-step basis or enhancing load to normal or beyond normal weight bearing levels.

EXAMPLE 2

This example shows a way to robotically measure limb movement characteristics of a spinal transected rat during locomotion training. Transections were performed five days after birth, as a more robust recovery of stepping occurs when transections are performed shortly after birth. The transected rat pup was returned to its mother until the pup reached 21 days of age. The rat was then trained two to three times a week for 5–10 minutes per day to perform bipedal, hindlimb stepping on a physical treadmill. Training consisted of manually holding the rats above a treadmill to allow a sufficient amount of loading on the hindlimbs. In this example, the rat was two months old, and could perform alternating, weight-bearing hindlimb stepping on a physical treadmill. However, the rat sometimes failed to initiate swing or dragged its toes during swing. All experiments followed the guidelines of the Animal Use Committee of the University of California, Los Angeles.

Each hindlimb of the rat was attached to a Phantom 1.0 robotic arm using a neoprene cuff placed around the hindlimb shank. The moving surface was provided by a conveyor belt moving at a speed of about 10 cm/s. The rat was physically held over the conveyor belt by a person, and stepping by the rat was induced by physically adjusting torso orientation and hindlimb loading. The Phantom 1.0 robotic arms did not apply force. Instead, the arms were moved passively by the hindlimbs. For each robotic arm, 3-D endpoint positions during one minute stepping bouts were sampled at about 100 Hz and stored on a computer. To analyze forces generated at the tip of the robotic arm, motor torque transformed to a spatial coordinate frame at the robotic arm endpoint was similarly sampled and stored.

Position trajectories of the robot end-effectors were analyzed to compare the quality of stepping. To quantify the periodicity of stepping, the power spectrums of the vertical position trajectories of both limbs during stepping were calculated using spectral estimation. To quantify interlimb phasing during stepping, the position trajectories of the two limbs were cross-correlated. Both the vertical and horizontal interlimb positions were correlated. Before correlation, the position data were filtered with a $9^{th}$ order Butterworth low-pass filter with a cutoff of 2.5 Hz (roughly twice the primary stepping frequency, as determined by the power spectral analysis).

Individual step height and stride lengths were calculated using the following algorithm. Stepping was assumed to yield a periodic vertical position trajectory where each period was analogous to one step. To find these periods, the vertical trajectories were low-pass filtered with the Butterworth filter at a cutoff frequency of 2.5 Hz, and the local maxima were located by searching for zero crossings (from positive to negative) in the corresponding velocity trajectory. An individual step was defined to occur between each of these peaks. The difference between the maximum and minimum value of the horizontal and vertical trajectories during one step period was defined as the step height and stride length of each step, respectively. Identified steps that had step heights smaller than an arbitrary cutoff of 5 mm or stride lengths smaller than 10 mm were discarded. The mean and standard deviation of stride length and step height of all steps taken by all rats on the virtual and physical treadmills, respectively, were calculated and compared using t-tests.

Hindlimb trajectories of a rat paw were determined. The average amplitudes of the trajectories were about 3.0 to about 4.0 cm in the horizontal direction, and about 1.5 to about 2.5 cm in the vertical direction.

EXAMPLE 3

Figure 12:
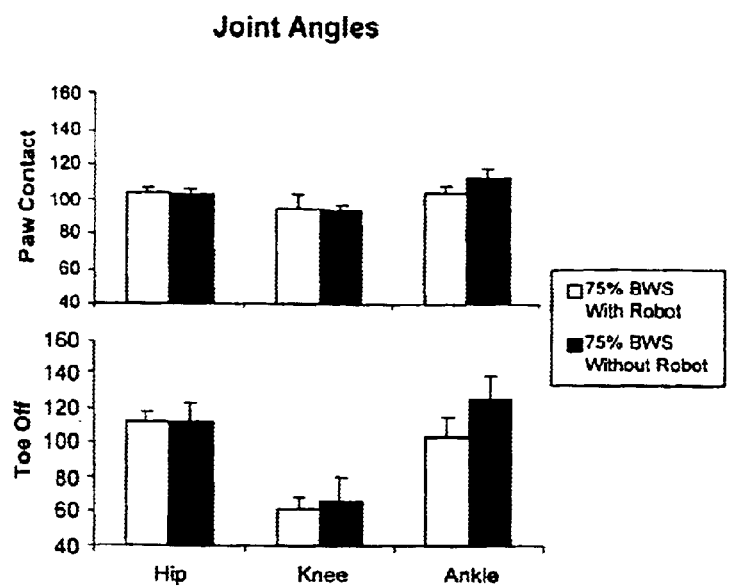
FIG. 12 is a bar graph showing the effect of robot attachment on rat joint angles during stepping.

This example shows that step cycle characteristics are not significantly altered by attachment of robotic arms to rat hindlimbs. Each hindlimb shank was attached to a Phantom 1.0 robotic arm using a neoprene cuff. Rats were suspended from a manually adjustable harness over a conveyor belt moving at a speed of about 11 cm/s. Body weight load was about 75%. Conventional kinematic film analysis was used to compare hip, knee and ankle joint angle displacements at various key points in the step cycle, such as toe off and paw contact, while rats stepped with and without the robotic arms attached. As shown in FIG. 12, hip and knee joint angles with attached robotic arms (white bars) were similar to the corresponding joint angles without attached robotic arms (black bars). For the ankle joint, only slightly greater flexion was apparent as a result of robotic arm attachment.

EXAMPLE 4

This example shows that the rat lumbar spinal cord responds to speed and load-related sensory information. Each hindlimb was attached to a Phantom 1.0 robotic arm using a neoprene cuff. Rats were supported over a moving conveyor belt by a manually adjustable counterweight system such as the one shown in FIG. 1. The rats were trained at two load levels about 50% and normal load—and two belt speeds—about 6 cm/s and about 20 cm/s. Kinematic data provided by the robotic system was used to quantify limb movement characteristics.

Figure 13:
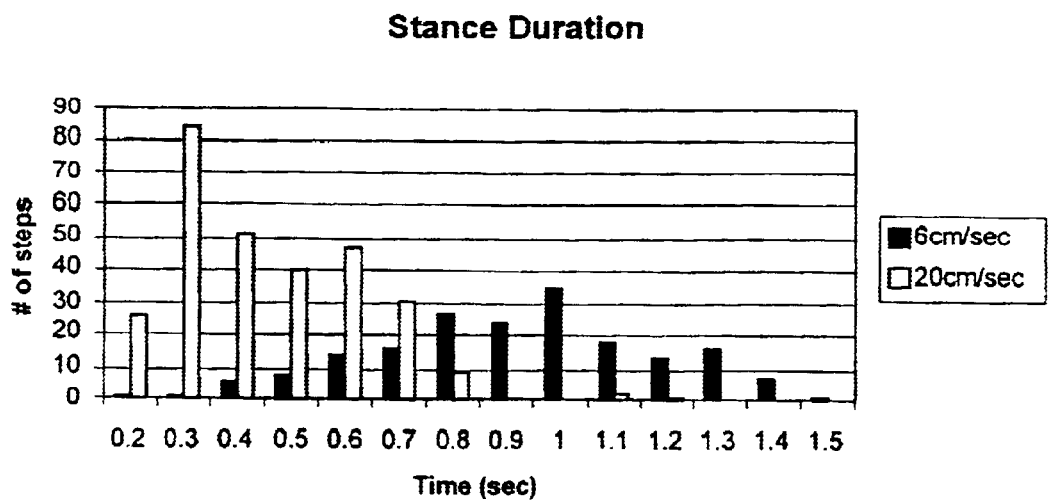
FIG. 13 is a histogram of stance duration of a representative rat at two treadmill speeds.
Figure 14:
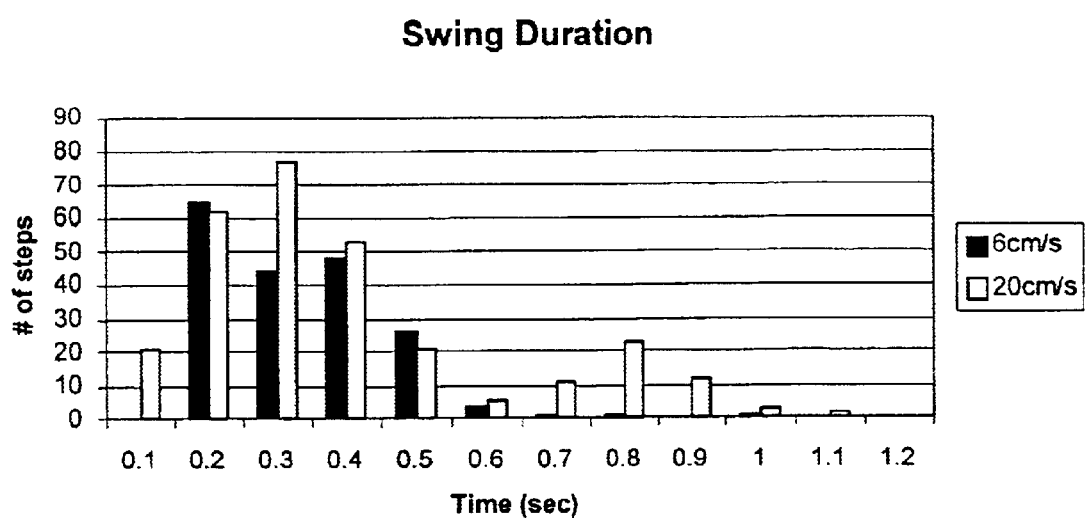
FIG. 14 is a histogram of swing duration of a representative rat at two treadmill speeds.
Figure 15:
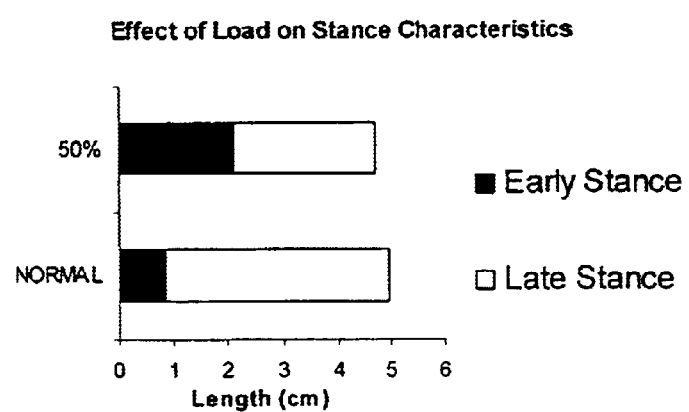
FIG. 15 is a bar graph showing the relative length of early and late stance for a rat at 50% load and normal load.

Stance duration results from one representative rat are shown in the histogram of FIG. 13, which records the number of steps having a particular stance duration during a training session. Stance duration at about 6 cm/s (black bars) was longer than stance duration at about 20 cm/s (white bars). Results from the same rat indicated that swing duration was unchanged at increasing speeds, as shown in FIG. 14. When load was increased from about half to normal weight bearing, the overall length of stance remained the same, but the length of early stance (black bars) decreased while the length of late stance (white bars) increased, as shown in FIG. 15, suggesting that greater loading on the hindlimbs enhanced the propulsion phase of stance.

EXAMPLE 5

This example shows a way to robotically apply vertical force to spinal transected rat hindlimbs. Each hindlimb was attached to a Phantom 1.0 robotic arm using a neoprene cuff. The rat was suspended over a moving conveyor belt as in Example 4. The robotic arms were programmed to apply a downward force, proportional to hindlimb velocity, on the lower shank when the limb moved backward, increasing load during stance. When the hindlimbs moved forward, the robotic arms were programmed to push the limb upward. Forces were applied during stance or swing, but not during both.

Figure 16:
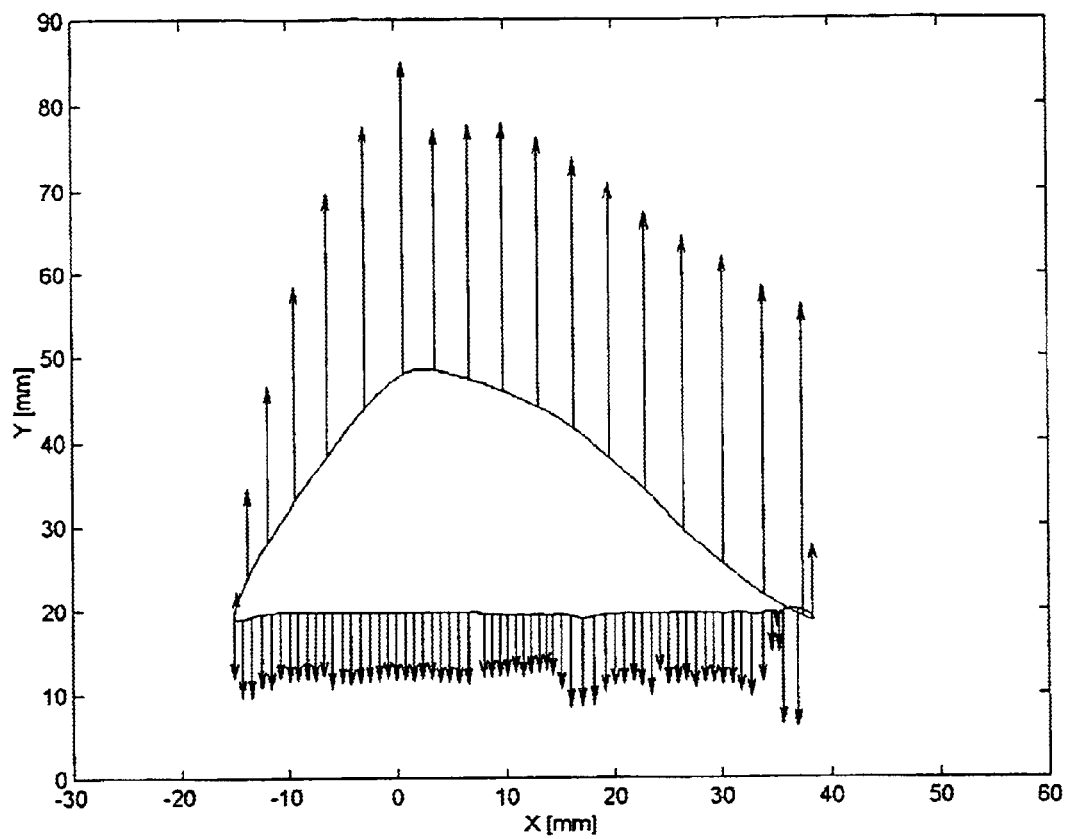
FIG. 16 is a graph of a single step cycle of a rat hindlimb showing the robotic forces applied during swing and stance.

A step cycle of one hindlimb is shown in FIG. 16. Robotically applied force during stance is shown by down-arrows in FIG. 16, while robotically applied force during swing is shown by up-arrows. Vertical force is proportional to horizontal velocity in FIG. 16. The forces are drawn at equivalent time intervals, illustrating changes in velocity.

When a downward force was applied to the limb during stance, the duration of stance decreased significantly, step frequency increased, and stride lengths and step heights decreased. When an upward force was applied to the limbs during the swing phase of stepping, there was initially a disruption of stepping evidenced by a longer swing duration and in-phase, hopping-like gait. However, over several trials and repetitive exposure to the force field stimuli, a normal pattern of stepping was recovered. These findings demonstrate that the robotic system can modulate sensory input into the spinal cord. Moreover, the spinal cord responds immediately to this modulation, and the response is detectable by the robotic mechanism.

EXAMPLE 6

This example shows a way to perform step training over a virtual surface. Each hindlimb of a spinal transected rat was attached to a Phantom 1.0 robotic arm using either a neoprene cuff, for attaching to metatarsus and lower shank, or a platform as shown in FIG. 5 for attaching to toes. Stepping was difficult to elicit by attaching to the toe or lower shank. Therefore, results were obtained by attaching to the metatarsus. The rat was physically held over the virtual surface by a person, and stepping by the rat was induced by physically adjusting torso orientation and hindlimb loading to engage the virtual surface.

The Phantom 1.0 robotic arms were programmed to emulate a virtual treadmill by creating a virtual block moving in the horizontal plane at a constant velocity. The "virtual block" enforced a one-sided spring-damper equation normal to the surface of the block to haptically simulate the presence of a solid object. The virtual treadmill block's stiffness and damping in the vertical plane was set to 1.0 N/mm to 0.005 N/m/s. The surface friction of the virtual treadmill was made infinite with a position-dependent velocity controller so that when the hindlimb extended at or below the plane of the virtual treadmill, the robot moved the limb backwards in a straight line under velocity control. A software option was added in which a virtual, vertical, planar constraint could be installed for each hindlimb so that the hindlimbs were restricted to preset sagittal planes and could not mechanically interfere with each other. Position trajectories, step height and stride lengths were calculated as in Example 1.

Hindlimb trajectories of a rat paw were measured. The average amplitudes in this example were about 3.0 cm to about 4.0 cm in the horizontal direction, and about 1.5 cm to about 2.5 cm in the vertical direction. Rats could step over the virtual moving surface. However, stepping was less consistent and not as sustained when compared to stepping over a physical treadmill surface, such as in Example 2. One reason for this result is that sensory information provided during stance and swing is critical for generating stepping in spinal animals. The physical treadmill configuration provided a more normal pattern of loading during stance since the toes were placed on an actual treadmill surface. Further, the physical treadmill configuration did not impose contact forces on the paws during swing since the robots were attached at the lower shank, not to the metatarsus. Moreover, improved loading during stance may have enhanced interlimb coordination and swing initiation, which resulted in more consistent stepping and greater swing height. In contrast, with the robots attached at the metatarsus in the virtual treadmill configuration, inappropriate sensory information was generated, and such information interfered with the execution of swing and stance.

EXAMPLE 7

This example provides additional ways to train rats over a virtual surface. Spinal transected rats were tested over a virtual treadmill generated as described in Example 6. Rat toes, heels and ankles were attached to platforms with adhesive tape. Initially, platforms were connected to robotic arms through a gimbal attached to a robotic arm end link rather than through the fixed joint 106 shown in FIG. 5. Rats were manually held above the virtual treadmill while stepping.

With rat toes attached to the platforms, rat hindlimbs flexed as rats were lowered toward the treadmill, and the treadmill would not engage to drive the hindlimbs backward. By placing weights on the platforms, it was determined that at least 17 grams of downward force were required to engage the treadmill owing to the friction in the robotic arm resisting both downward and backward movement. Other problems were that the weight of the gimbal itself was enough to invert rat ankles, resulting in an abnormal walking position, and a rat's hindlimbs would sometimes move close to enough to each other to cause the robotic arms to physically interfere with each other, thus disrupting cyclic movement.

Based on these results, several changes in design were made. The need for increased friction was addressed by replacing the existing virtual treadmill controller with a position-dependent velocity controller. A virtual, vertical, planar constraint could be installed for each hindlimb so that the hindlimbs were restricted to preset sagittal planes and could not mechanically interfere with each other. The gimbal frame was counterbalanced such that its weight would not apply moments to rat paws. Finally, the gimbal's degrees of freedom were removed by constraining them with adhesive tape.

A rat tested with the modified system engaged the treadmill, but the gimbals continued to cause the rat's ankles to invert. The gimbals' degrees of freedom were again removed using tape. The rat was then able to achieve rhythmic stepping. However, the stepping was sporadic and difficult to evoke in comparison with stepping on a physical treadmill.

To further improve rat training, stepping with robotic arms attached to rat heels was compared to stepping with robotic arms attached to toes. In these tests, the gimbals were removed and replaced by fixed joints.

To compensate for inertia, robotic arm inertia was estimated by assuming the robotic arm acted as a simple mass in the workspace region where stepping occurred. To identify this mass, the robot endpoint was moved in a sinusoidal trajectory in the horizontal and then vertical plane. The motor forces were recorded, and the acceleration of the endpoint was calculated by double-differencing the position trajectory. Acceleration was plotted against motor force, and the linearized inertia of the robot arm was estimated using the slope of this relationship. The estimated inertia was about 42 grams in the vertical plane, and about 75 grams in the horizontal plane.

To estimate static friction, the motors were programmed to apply a ramp force with the robot arm in the center of the stepping workspace, and the force at which the robotic arm began moving was measured. The static friction in the horizontal and vertical planes was about 0.17 N and about 0.05 N, respectively.

Based on these estimates, the robotic arms were programmed to apply assistive forces to compensate for inertia and friction. The inertia-compensating force was calculated by multiplying the estimated inertial by the robot endpoint acceleration, low pass filtered at 6 Hz. With this approach, the robot remained stable with compensation of up to about 60% of the estimated inertia. The friction-compensating force was equal to the estimated static friction, applied in the direction of motion of the robot endpoint.

Stepping ability was tested using friction and inertia compensation. With attachment to rat toes, short sequences of steps were elicited, but alternating gait was not sustained for more than several strides during an hour testing period. With attachment to the heels, longer sequences of consistent stepping was achieved accompanied by smooth swing trajectories at near normal stride lengths for up to twenty strides.

EXAMPLE 8

This example shows a way to train rats at varying load conditions. Adjusting weight support to provide the maximal possible loading on a step-by-step basis may produce an optimal pattern of load-related sensory input that is necessary for learning to step. Weight support can be provided by an automatically adjusting body weight suspension assembly such as the motorized system or the spring-actuated system described herein. Rats can be trained to perform bipedal hindlimb stepping on a treadmill under one of the three weight-support conditions: fixed weight support, weight support adapted at the beginning of each session, and weight support adapted step-by-step.

FIXED WEIGHT SUPPORT. For this group, about 75% of the weight of the animal can be supported, thus the limbs can bear about 25% of the body weight (i.e. half of normal load level on hindlimbs). The animals can receive this fixed level of weight support for the entire training period (8 weeks). This weight support level is sufficient to generate a significant training effect.

WEIGHT SUPPORT ADAPTED AT THE BEGINNING OF EACH SESSION. For this group, the minimal amount of weight support that can be provided to generate stepping can be determined before each training session begins. Stepping initially can be generated while most of the weight of the animal (about 85%) is supported. A computer algorithm can then decrease weight support gradually at a fixed rate (dW) until the minimal level of support is reached at which the animal is still able to execute a minimum number (N) of consecutive steps with adequate hindlimb extension (E) measured with the robotic system as the mean distance between the lower shank and hip). Once determined, this minimal weight support level can be used for the entire training session. Appropriate values for the parameters dW, N, and E can be determined in a series of preliminary experiments with a separate group of animals before beginning training.

WEIGHT SUPPORT ADAPTED STEP-BY-STEP. For this group, the amount of weight support can be continuously monitored and adjusted within each training session using a computer algorithm. The objective is to load the limbs with as much weight bearing as possible without causing the rat to collapse. Ongoing stepping performance can be monitored in real time using the kinematic data provided by the robotic system, and steps can be counted using step-detecting software that monitors the movement ranges of the lower shank. The computer algorithm can set the weight support level initially at about 75%, and can gradually decrease the level at a fixed rate (dW). If the software detects a cessation in stepping or inadequate hindlimb extension (E, measured with the robotic system as the mean distance between the lower shank and hip), it gradually increases the weight support level at a fixed rate (dU) until a minimum of number (N) sequential successful steps is executed. When consistent stepping resumes, the software again decreases the weight-support level at dW. Appropriate values for the parameters dW, dU, E, and N are determined in a series of preliminary experiments with a separate group of animals before beginning training.

Locomotor testing with data acquisition/analyses can be performed to quantify recovery characteristics. Characteristics can include number of steps performed at a given treadmill speed-weight support level, rate of recovery of normal or greater than normal weight-bearing, amount of electromyographic activity in the soleus extensor muscles of both hindlimbs, and amount of hindlimb extension during stance, e.g. hip, knee, ankle angles and lengths of early, late stance.

EXAMPLE 9

This example shows a way of determining the effects of loading on locomotor recovery. Rats can be suspended over a treadmill with weight support provided by the automatically adjusting body weight suspension assembly described herein. Each hindlimb shank can be connected to a robotic arm using neoprene cuffs. Loading the hindlimbs beyond normal weight-bearing levels may enhance load-related sensory information and facilitate the acquisition of stepping by the lumbar spinal cord.

The amount of weight support provided by the suspension assembly can be adjusted to provide 50% of normal weight bearing by the hindlimbs. Then the robotic arms can be programmed to provide additional loading on the ankle and paw by exerting a downward force on the shank. Spinal transected rats can be trained in one of three groups: 50% normal load, 100% normal load, and 200% normal load.

50% NORMAL LOAD. The weight support system is set to deliver 50% normal load, and the robotic arms do not provide any additional force to the hindlimbs.

100% NORMAL LOAD. For this group, the robot arms push the limbs down during stance to provide additional load equivalent to 100% normal load on the hindlimbs. Therefore they supplement the load delivered through the body weight support system by another 50% of normal load.

200% NORMAL LOAD. The robot arms enhance the loading during stance to 200% normal load on the hindlimbs.

Loading can be achieved by using the robotic arms to apply a downward force on the lower shank proportional to hindlimb velocity while the hindlimb moves backward along the treadmill. By adjusting the gain, 100% or 200% load can be achieved. Since the hindlimb moves at nearly a constant velocity on the treadmill, an approximately constant downward force can be applied. The constant downward force provide smooth transitions in force application at the beginning and end of stance when the hindlimb reverses movement direction.

Locomotor testing with data acquisition/analyses can be performed to quantify recovery characteristics. Characteristics can include number of steps performed at a given treadmill speed-weight support level, rate of recovery of normal or greater than normal weight-bearing, amount of electromyographic activity in the soleus extensor muscles of both hindlimbs, and amount of hindlimb extension during stance, e.g. hip, knee, ankle angles and lengths of early, late stance.

EXAMPLE 10

This example shows a way to determine the effects of alternating versus in-phase gait training on locomotor recovery of spinal transected rats. Rats can be suspended over a treadmill and connected to robotic arms as in Example 9. The robotic arms can be programmed to impose one of three patterns of coordination in the hindlimbs: alternating gait, in-phase gait, and no-assistance.

ALTERNATING GAIT. For this group, the robotic arms can impose an alternating gait in the hindlimbs based on the period of double support, i.e. period of time when the two hindlimbs are weight-bearing. Normal periods of double support indicate that the limbs are performing stable walking with alternating movements in the two hindlimbs, whereas shorter double support periods are associated with step failures and stumbling in spinal animals. The robotic arms can be programmed to maintain a normal double support period that is appropriate for walking at a moderate treadmill speed (about 11 cm/s). If the robots sense that the double support period is too short, forward swing of the trailing hindlimb can be accelerated by the robotic arms to correct double support duration. The normal range of double support periods can be determined in preliminary experiments performed before beginning locomotion training.

IN-PHASE GAIT. The robotic arms can impose an in-phase gait at about 11 cm/s, i.e. move the two hindlimbs to execute a hopping gait on the treadmill. The robotic arms can be programmed to initiate forward swing in one hindlimb as soon as the opposite hindlimb has begun forward swing. The beginning of stance in the two hindlimbs can be synchronized by the robotic arms by driving the trailing limb to the treadmill as soon as the other limb initiates stance.

NO-ASSISTANCE. The robotic arms can be attached passively without applying forces to affect coordination. Stepping can be trained at the same treadmill speed (about 11 cm/s) as in the other two groups.

Locomotor testing with data acquisition/analyses can be performed to quantify recovery characteristics. Characteristics can include number of steps performed at a given treadmill speed-weight support level, double support duration, x and y position correlation, and phasing of ipsilateral/contralateral electromyographic activity in the soleus extensor and tibialis anterior flexor muscles.

EXAMPLE 11

This example shows a way to demonstrate that the lumbar spinal cord adapts to the levels of mechanical assistance used to facilitate stepping movements during locomotor training. Rats can be suspended over a treadmill and connected to robotic arms as in Example 9. During training, mechanical assistance can be provided under one of three conditions: no-assistance, fully-assisted, and assist-as-needed.

NO ASSISTANCE. For this group, weight-bearing stepping movements can be elicited by placing the rat's hindlimbs on the treadmill with the robotic arms attached but not controlling hindlimb movements.

FULLY-ASSISTED. The hindlimbs can be driven by the robotic arms along normal, coordinated stepping trajectories, regardless of the muscle activity generated by the spinal cord.

ASSIST-AS-NEEDED. The robotic arms can intelligently assist hindlimb movements during the step cycle using a combination of the training strategies described in Examples 8, 9 and 10.

For the fully-assisted group, the robotic arms can move the hindlimbs along fixed trajectories identical to mean trajectories identified from intact rats. Mean trajectories can be determined in preliminary experiments performed before beginning step training. A high-gain position-derivative controller can be used to move the hindlimbs along the desired normal trajectories.

During "assist-as-needed" training, the techniques described in Examples 8, 9 and 10 can be applied in combination. Specifically, rats in this group can receive continually adapting body weight support according to the algorithm described in Example 8 such that the rats are provided with just enough support to maintain stepping. In addition, rats can receive additional loading of the ankle and paw through the robotic arm using the technique described in Example 9. The loading can be adjusted on a step-by-step basis so that total loading on the hindlimb equals the loading level found most effective in studies carried out as in Example 9. Therefore, if the target support level is WT, the weight support system provides WS(t) as a function of time t, and the robot applies WR(t) through the shank, then the computer will set WR(t)=WT−WS(t), so that WR(t)+WS(T)=WT. Consequently, as the animal achieves greater load bearing, the robotic loading through the shank can be decreased. Total loading provided through the weight support system and the robotic arms can be adjusted as needed to achieve the target loading level. In addition the robotic arms can assist in maintaining normative double support time as needed for each treadmill training speed using the techniques described in Example 10.

Locomotor testing with data acquisition/analyses can be performed to quantify the number of steps performed at a given treadmill speed-weight support level.

REFERENCES

1. Aisen, M. L., Krebs, H. I., Hogan, N., McDowell, F. and Volpe, B. T. The effect of robot-assisted therapy and rehabilitative training on motor recovery following stroke. *Arch. Neurol.* 54: 443–445 (1997).
2. Barbeau, H. and Rossignol, S. Recovery of locomotion after chronic spinalization in the adult cat. *Brain Res.* 412: 84–95 (1987).
3. Barbeau, H; Norman, K; Fung, J; Visintin, M; Ladouceur, M. Does neurorehabilitation play a role in the recovery of walking in neurological populations? *Annals of the New York Academy of Sciences* 860: 377–92 (1998).
4. Behrman, A. L. and Harkema, S. J. Locomotor recovery after human spinal cord injury: a series of case studies. *Physical Therapy.* 80:688–699 (2000).
5. Bejczy, A. Towards Development of Robotic Aid for Rehabilitation of Locomotion-impaired Subjects. *Proc. of 1st Workshop on Robot Motion and Control (RoMoCo),* Kiekrz, Poland, 9–16 (1999).
6. Belanger, M., Drew, T., Provencher, J., and Rossignol, S. A comparison of treadmill locomotion in adult cats before and after spinal transection. *J. Neurophysiol.* 76: 471–491 (1996).
7. Colombo, G., Joerg, M., Schreier, R. and Dietz, V. Treadmill training of paraplegic patients using a robotic orthosis. *J. Rehab. Research and Development,* 37: 693–700 (2000).
8. de Guzman, C. P., Roy, R. R., Hodgson, J. A., and Edgerton, V. R. Coordination of motor pools controlling the ankle musculature in adult spinal cats during treadmill walking. *Brain Res.* 555: 202–214 (1991).
9. de Leon R. D., London, N. J. S., Roy, R. R., Edgerton, V. R. Failure analysis of stepping in adult spinal cats. In: Peripheral and Spinal Mechanisms in the Neural Control of Movement: Progress in Brain Research, M. D. Binder (ed.), Elsevier Science B. V., Netherlands, 123: Chapter 30, 341-348 (1999).
10. de Leon R. D., Timoszyk W. K., Joynes R., Roy R. R., Reinkensmeyer D. J., Edgerton V. R. Using robots to train spinally-transected rats to recover hindlimb stepping. *Society for Neuroscience Abstracts*, Nov. 10–15, 260.14 (2000).
11. de Leon, R., Hodgson, J. A., Roy, R.R., and Edgerton, V. R. Extensor- and flexor-like modulation within motor pools of the rat hindlimb during treadmill locomotion and swimming. *Brain Res.* 654: 241–250 (1994).
12. de Leon, R. D., Hodgson, J. A., Roy, R. R., and Edgerton, V. R. Full weight-bearing hindlimb standing following stand training in the adult spinal cat. *J. Neurophysiol.* 80: 83–91 (1998).
13. de Leon, R. D., Hodgson, J. A., Roy, R. R., and Edgerton, V. R. Hindlimb locomotor and postural training modulates glycinergic inhibition in the spinal cord of the adult spinal cat. *J. Neurophysiol* 82: 359–369, (1999).
14. de Leon, R. D., Hodgson, J. A., Roy, R. R., and Edgerton, V. R. Locomotor capacity attributable to step training versus spontaneous recovery following spinalization in cats. *J. Neurophysiol.* 79:1329–1340 (1998).
15. de Leon, R. D., Hodgson, J. A., Roy, R. R., and Edgerton, V. R. The retention of hindlimb stepping ability in adult spinal cats after the cessation of step training. *J. Neurophysiol.* 81: 85–94 (1999).
16. de Leon, R. D., Huang, J. T., Wilson, W. M., Hodgson, J. A., Roy, R. R., Garfinkel, A. and Edgerton, V. R. The effects of quipazine (i.t. and i.p.) on the locomotor and postural capabilities of trained and non-trained spinal transected adult rats. *Soc. Neurosci. Abstr.* 21: 421 (1995).
17. de Leon, R. D., Timoszyk, W., London, N., Joynes, R. L., Roy, R. R., Reinkensmeyer, D. J., Edgerton, V. R. Locomotor adaptations to Robot-applied force fields in spinally transected rats. *Soc. Neurosci. Abstr.* 26: 697 (2000).
18. Dietz, V., Wirz, M., Colombo, G., and Curt, A. Locomotor capacity and recovery of spinal cord function in paraplegic patients: a clinical and electrophysiological evaluation. *Electroenceph. and Clin. Neurophys.* 109: 140–153 (1998).
19. Dietz, V; Wirz, M; Curt, A; Colombo, G. Locomotor pattern in paraplegic patients: training effects and recovery of spinal cord function. *Spinal Cord* 36(6): 380–90 (1998).
20. Dobkin, B. H. Neurologic Rehabilitation (F.A. Davis Company, Philadelphia, 1996).
21. Dobkin, B. H., Harkema, S., Requejo, P., and Edgerton, V. R. Modulation of locomotor-like EMG activity in subjects with complete and incomplete spinal cord injury. *J. Neuro. Rehab.* 9: 183–190 (1995).
22. Edgerton, V. R., de Leon, R. D., Tillakaratne, N., Recktenwald, M. R., Hodgson, J. A., and Roy R. R. Use-dependent plasticity in spinal stepping and standing. In: Advances in Neurology: Neuronal Regeneration, Reorganization and Repair, Philadelphia, Lippincott-Raven Publishers, 1997, pp. 233–247.
23. Edgerton, V. R., Roy, R. R., de Leon, R., Tillakaratne, N., and Hodgson, J. A. Does motor learning occur in the spinal cord? *Neuroscientist* 3: 287-294 (1997).
24. Edgerton, V. R., Roy, R. R., Hodgson, J. A., Gregor, R. J., and de Guzman, C. P. Recovery of full weight-supporting locomotion of the hindlimbs after complete thoracic spinalization of adult and neonatal cats. In: Restorative Neurology, Plasticity of Motoneuronal Connections. New York, Elsevier Publishers, 1991, pp. 405–418.
25. Finch, L. and Barbeau, H. Hemiplegic gait; new treatment strategies. *Physiotherapy Canada.* 38: 36–41 (1986).
26. Fung, J., Stewart, J. E., Barbeau, H. The combined effects of clonidine and cyrpheptadine with interactive training on the modulation of locomotion in spinal cord injured subjects. *J. Neurol. Sci.* 100: 85–93 (1990).
27. Gardner, M. B., Holden, M. K., Leikauskas, J. M. and Reginald, R. L. Partial body weight support with treadmill locomotion to improve gait after incomplete spinal cord injury: a single subject experimental design. *Physical Therapy.* 78:361–374 (1998).
28. Gazzani, F., Bernardi, M., Macaluso, A., Coratella, D., Ditunno, J. F., Castellano, V., Torre, M., Macellari, V. and Marchetti, M. Ambulation training of neurlogical patients on the treadmill with a new walking assistance and rehabilitation device (WARD). *Spinal Cord.* 37: 336–344 (1999).
29. Goslow, GE Jr; Reinking, RM; Stuart, DG. The cat step cycle: hind limb joint angles and muscle lengths during unrestrained locomotion. *Journal of Morphology,* 141(1):1–41 (1973).
30. Grau, J. W., Barstow, D. G., Joynes, R. L. Instrumental learning within the spinal cord: I. Behavioral properties. *Beh. Neurosci.* 112: 1366–86 (1998).
31. Harkema, S. J., Hurley, S. L., Patel, U. K., Requejo, P. S., Dobkin, B. H., and Edgerton, V. R. Human lumbosacral spinal cord interprets loading during stepping. *J. Neurophysiol.* 77: 797–811 (1997).
32. Hesse, S. and Uhlenbrock, D. A mechanized gait trainer for restoration of gait. *J. Rehab. Research and Development,* 37: 701–708 (2000).
33. Hesse, S., Uhlenbrock, D. and Sarkodie-Gyan, T. Gait pattern of severely disabled hemiparetic subjects on a new controlled gait trainer as compared to assisted treadmill walking with partial body weight support. *Clinical Rehabilitation* 13: 401–410 (1999).
34. Hesse, S. A. et al., Gait outcome in ambulatory hemiparetic patients after a 4-week comprehensive rehabilitation program and prognostic factors. *Stroke* 25: 1999–2004 (1994).
35. Hesse, S. A. et al., Restoration of gain pattern in nonambulatory hemiparetic patients by treadmill training with partial body-weight support. *Arch Phys Med Rehabil* 75: 1087–1093 (1994).
36. Hiebert, GW; Pearson, KG. Contribution of sensory feedback to the generation of activity during walking in the decerebrate Cat. *Journal of Neurophysiology,* 81(2):758–70 (1999).
37. Hodgson, J. A., Roy, R. R., de Leon, R., Dobkin, B., and Edgerton, V. R. Can the mammalian lumbar spinal cord learn a motor task? *Med. Sci. Sports Exerc.* 26: 1491–1497 (1994).
38. Hogan, N.; Lemay, M. A., Ren, T.-M.; Abu-Khalil, R. K., Charette, M. F., Finklestein, S. P. Automated assay of functional motor recovery due to intracisternal growth factors. *Society for Neuroscience Abstracts* 24 (1–2): 1950 (1998).
39. Kim, D; Adipudi, V; Shibayama, M; Giszter, S; Tessler, A; Murray, M; Simansky, K J. Direct agonists for serotonin receptors enhance locomotor function in rats that received neural transplants after neonatal spinal transection. *Journal of Neuroscience,* 19(14):6213–24 (1999).

40. London, N. J. S., R. D. de Leon, D. J. Reinkensmeyer, W. K. Timoszyk, R. R. Roy, V. R. Edgerton. Using Robots to train spinally-transected rats to recover hindlimb stepping. *Soc. Neurosci. Abstr.* 26: 697 (2000).

41. Lovely, R. G., Gregor, R. J., Roy, R. R., and Edgerton, V. R. Effects of training on the recovery of full weight-bearing stepping in the adult spinal cat. *Exp. Neurol.,* 92: 421–435 (1986).

42. Lovely, R. G., Gregor, R. J., Roy, R. R., and Edgerton, V. R. Weight-bearing hindlimb stepping in treadmill-exercised adult spinal cats. *Brain Res.,* 514: 206–218 (1990).

43. Lum, P. S., Burgar, C. G., and Van der Loos, H. F. M. "The use of a robotic device for post-stroke movement therapy," Proc. Int. Conf. Rehab. Robotics, Bath, U.K., Apr. 14–15, (1997).

44. Miya, D., Giszter, S., Mori, F., Adipudi, V., Tessler, A., and Murray, M. Fetal transplants alter the development of function after spinal cord transection in newborn rats. *J. Neurosci.* 17: 4856–4872 (1997).

45. Pratt, C. A., Fung, J., and Macpherson, J. M. Stance control in the chronic spinal cat. *J. Neurophysiol.* 71: 1981–1985 (1994).

46. Reinkensmeyer, D., Kahn, L., Averbach, M., McKenna, A., Schmit, B., and Rymer, W. Understanding and promoting arm movement recovery after chronic brain injury: Progress with the ARM Guide. *J. Rehab. Res. Dev.* 37: 653–662 (2000).

47. Reinkensmeyer, D. J., Hogan, N., Krebs, H. I., Lehman, S. L., and Lum, P. S. Rehabilitators, robots, and guides: New tools for neurological rehabilitation, p. 516–533 in Biomechanics and Neural Control of Movement, ed. Jack Winters and Pat Crago, Springer-Verlag, 2000.

48. Reinkensmeyer, D. J., Timoszyk, W. K., de Leon, R. D., Joynes, R., Kwak, E., Minakata, K., Edgerton, V. R. A robotic stepper for retraining locomotion in spinal-injured rodents. Proceedings of the 2000 IEEE International Conference on Robotics & Automation, San Francisco, Calif., April, pp. 2889–2894 (2000).

49. Reinkensmeyer, D. J., Timoszyk, W. K, de Leon, R. D., London, N., Joynes, R., Roy, R. R. and Edgerton, V. R. Robotic quantification of stepping by spinally-transected rats: comparison of virtual and physical treadmill approaches. *Soc. Neurosci. Abstr.* 26: 697, (2000).

50. Stelzner, D. J., Ershler, W. B., and Weber, E. D. Effects of spinal transection in neonatal and weanling rats: survival of function. *Exp. Neurol.* 46: 156–177 (1975).

51. Talmadge, R. J., Roy, R. R., and Edgerton, V. R. Alterations in the glycinergic neurotransmitter system are associated with stepping behavior in neonatal spinal cord transected rats. *Soc. Neurosci. Abstr.* 22: 1397 (1996).

52. Tillakaratne, N. J. K., Hodgson, J. A., Roy, R. R., Tobin, A. J. and Edgerton, V. R. Spinally transected adult cats show changes in glutamate decarboxylase (GAD67) mRNA in lumbar spinal cord after locomotor or standing training. *Soc. Neurosci. Abstr.* 21: 380 (1995).

53. Visintin, M. and Barbeau, H. The effects of body weight support on the locomotor pattern of spastic paretic patients. *Can J Neurol Sci* 16: 315–325 (1989).

54. Wernig, A. and Muller S. Improvement of walking in spinal cord injured persons after treadmill training. *Plasticity of Motoneural Connections*; A. Wernig (Elsevier Science Publications, 1991).

55. Wernig, A. and Muller, S. Laufand locomotion with body weight support improved walking in persons with severe spinal injuries. *Paraplegia* 30: 229–38 (1992).

56. Wernig, A., Muller, S., Nanassy, A., and Cagol, E. Laufband (treadmill) therapy based on "rules of spinal locomotion" is effective in spinal cord injured persons. *Eur. J. Neurosci.* 7: 823–829 (1995).

57. Wernig, A., Nanassy, A., and Muller, S. Laufband (treadmill) therapy in incomplete paraplegia and tetraplegia. *J. Neurotrauma.* 16: 719–726 (1999).

58. Wickelgren, I. Teaching the spinal cord to walk. *Science* 279: 319–321 (1998).

59. Zhang, A. A., Kirkpatrick, G., Zhong, V. H., Nguyen, V. T., Dobkin, B. H., and Edgerton, V. R. Cinematographic analysis of hindlimb stepping in spinal (7 day post-natal) rats. *Soc. Neurosci. Abstr.* 20: 571 (1994).

60. Zhang, A. A., Nishizono, H., de Leon, R., Master, J. K., Wu, M., Pai, A., Kailes, S., Dobkin, B. H., and Edgerton, V. R. Cinematographic analysis of hindlimb modulated by quipazine and strychnine in the adult spinal rat. *J Neurotrauma* 11: 132 (1994).

What is claimed is:

1. A system for locomotion assessment and training of a rodent-sized mammal, comprising:

(a) a moving surface;

(b) a suspension assembly for suspending the mammal over the moving surface so that one or more limbs of the mammal contact the moving surface; and (c) a robotic force applicator for connecting to and applying force to the one or more limbs that contact the moving surface.

2. The system of claim 1 in which the mammal is an animal about the size of a rat.

3. The system of claim 1 in which the suspension assembly comprises a counterweight support system.

4. The system of claim 1 in which the suspension assembly comprises an automatically adjustable motorized support system.

5. The system of claim 1 in which the robotic force applicator comprises one or more robotic arms.

6. The system of claim 1 in which the mammal is a laboratory rodent.

7. A system for locomotion assessment and training of a rodent-sized mammal, comprising:

(a) a moving surface;

(b) a suspension assembly for suspending the mammal over the moving surface so that one or more limbs of the mammal contact the moving surface; and (c) a robotic measuring assembly for connecting to the one or more limbs of the mammal and for measuring limb movement characteristics of the mammal suspended over the moving surface.

8. The system of claim 7 in which the mammal is an animal about the size of a rat.

9. The system of claim 7 in which the suspension assembly comprises a counterweight support system.

10. The system of claim 7 in which the suspension assembly comprises an automatically adjustable motorized support system.

11. The system of claim 7 in which the robotic measuring assembly comprises one or more robotic arms.

12. The system of claim 7, further comprising a robotic force applicator for applying force to the one or more limbs that contact the moving surface.

13. The method of claim 7 in which the mammal is a laboratory rodent.

14. A system for locomotion assessment and training of a laboratory rodent, comprising:

(a) a moving surface;

(b) a suspension assembly for suspending the rodent over the moving surface so that both rodent hindlimbs contact the moving surface; and (c) a robotic mechanism for applying force to the hindlimbs and for measuring limb movement characteristics of the rodent suspended over the moving surface, the robotic mechanism comprising two robotic arms, one arm for each hindlimb, each arm having at least two degrees of freedom.

15. The system of claim 14 in which the suspension assembly comprises a counterweight support system.

16. The system of claim 14 in which the suspension assembly comprises an automatically adjustable motorized support system.

17. The system of claim 14 in which the suspension assembly comprises a spring-actuated support system.

18. The system of claim 14 in which the suspension assembly comprises a spring-actuated support system.

19. A method of locomotion assessment and training of a rodent-sized mammal, comprising the steps of:
    (a) providing a moving surface;
    (b) suspending the mammal over the moving surface so that one or more limbs of the mammal contact the moving surface;
    (c) connecting a robotic force applicator to the one or more limbs that contact the moving surface; and
    (d) applying robotically produced force to the one or more limbs that contact the moving surface.

20. The method of claim 19 in which the mammal is an animal about the size of a rat.

21. The method of claim 19 in which the mammal is a laboratory rodent.

22. A method of locomotion assessment and training of a rodent-sized mammal, comprising the steps of:
    (a) providing a moving surface;
    (b) suspending the mammal over the moving surface so that one or more limbs of the mammal contact the moving surface;
    (c) connecting a robotic measuring assembly to the one or more limbs that contact the moving surface; and
    (d) robotically measuring limb movement characteristics of the mammal suspended over the moving surface.

23. The method of claim 22 in which the mammal is an animal about the size of a rat.

24. The method of claim 22, further comprising the step of applying robotically produced force to the one or more limbs that contact the moving surface.

25. The method of claim 22 in which the mammal is a laboratory rodent.

26. A method of locomotion assessment and training of a laboratory rodent, comprising the steps of:
    (a) providing a moving surface;
    (b) suspending the rodent over the moving surface so that one or both rodent hindlimbs contact the moving surface;
    (c) connecting a robotic force applicator to the one or both hindlimbs that contact the moving surface; and
    (d) applying robotically produced force to the one or both hindlimbs that contact the moving surface.

27. The method of claim 26 in which the surface is moving at a speed ranging from about 6 cm/s to about 20 cm/s.

28. The method of claim 26 in which load on the rodent ranges from about 25% to about 100% of body weight.

29. A method of locomotion assessment and training of a laboratory rodent, comprising the steps of:
    (a) providing a moving surface;
    (b) suspending the rodent over the moving surface so that both rodent hindlimbs contact the moving surface;
    (c) connecting a robotic measuring assembly to the one or both hindlimbs that contact the moving surface; and
    (e) robotically measuring limb movement characteristics of the rodent suspended over the moving surface.

30. The method of claim 29 in which the surface is moving at a speed ranging from about 6 cm/s to about 20 cm/s.

31. The method of claim 29 in which load on the rodent ranges from about 25% to about 100% of body weight.

32. The method of claim 29, further comprising the step of applying robotically produced force to the one or both hindlimbs that contact the moving surface.

* * * * *